United States Patent [19]

Privalov

[11] 4,333,332
[45] Jun. 8, 1982

[54] DIFFERENTIAL SCANNING MICROCALORIMETER

[76] Inventor: Peter L. Privalov, ulitsa Obrucheva, 28, korpus 2, kv. 145, Moscow, U.S.S.R.

[21] Appl. No.: 152,140

[22] Filed: May 21, 1980

[30] Foreign Application Priority Data

May 21, 1979 [SU] U.S.S.R. .............................. 2760252

[51] Int. Cl.³ ............................................ G01N 25/20
[52] U.S. Cl. ...................................................... 374/10
[58] Field of Search ............................ 73/15 B, 190 R

[56] References Cited

U.S. PATENT DOCUMENTS

| 3,267,728 | 8/1966 | Solomons | 73/190 R |
| 3,675,465 | 7/1972 | Sommer et al. | 73/15 B |
| 3,726,644 | 4/1973 | Desnoyers et al. | 73/190 R X |

Primary Examiner—Jerry W. Myracle
Attorney, Agent, or Firm—Myron Greenspan

[57] ABSTRACT

A differential scanning microcalorimeter comprises an adiabatic shell accommodating two capillary calorimetric chambers. One end of each chamber extends beyond the shell and passes through a heat bypass. At least one chamber is contrived in the form of two capillary tubes in thermal contact with each other, with the ends located inside the shell communicating with an end of the other chamber also located inside the shell.

5 Claims, 4 Drawing Figures

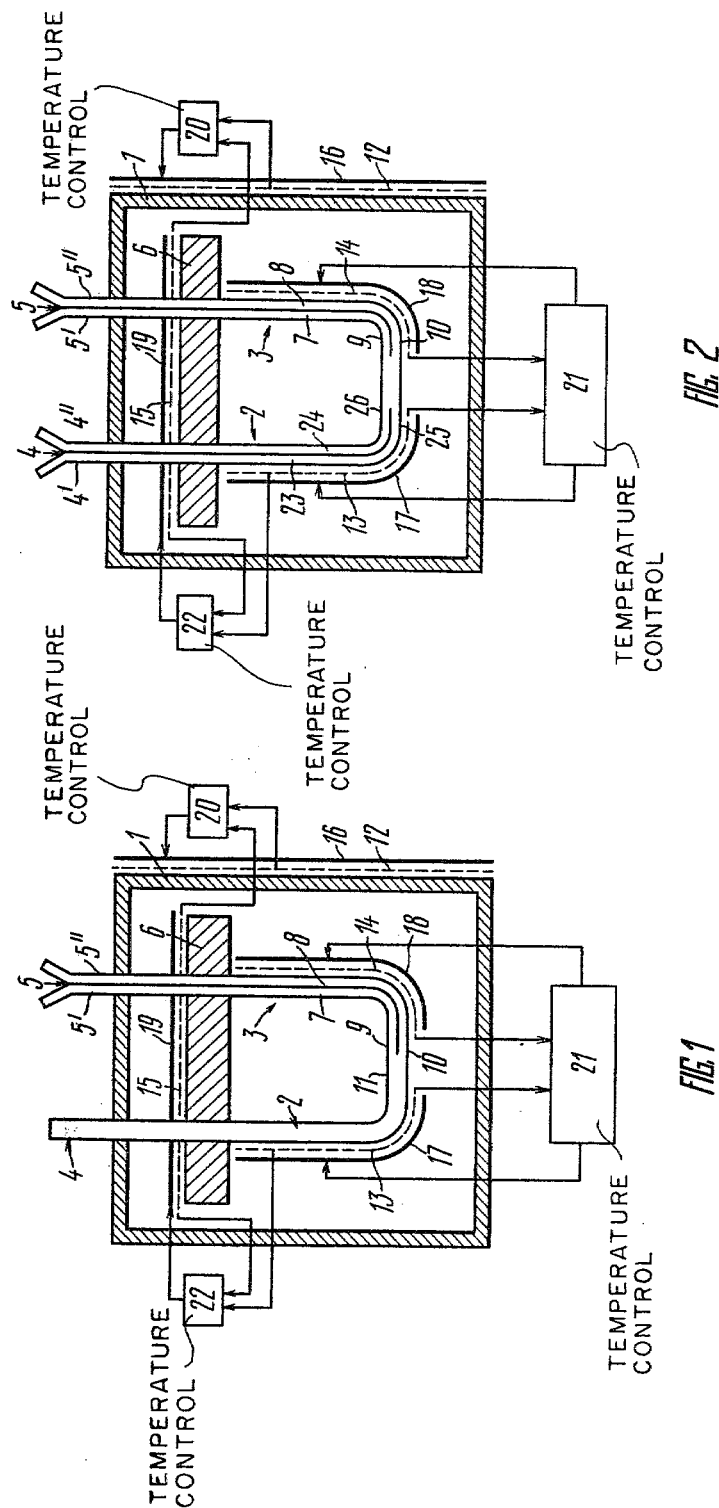

DIFFERENTIAL SCANNING MICROCALORIMETER

FIELD OF THE INVENTION

The present invention relates to microcalorimeters, and, more specifically, to differential scanning microcalorimeters.

The invention can be applied in laboratories for examination of liquid media.

BACKGROUND OF THE INVENTION

Known in the art is a differential scanning microcalorimeter, the adiabatic shell of which accommodates two capillary calorimetric chambers, the ends extending from the adiabatic shell passing through a heat bypass serving for limiting the working volumes of the chambers, with external surfaces of the adiabatic shell, capillary calorimetric chambers and heat bypass mounting thermal sensing elements and heating elements electrically coupled with temperature controls (cf. U.S. Pat. No. 3,899,918, cl. 73-15B, 1975).

The capillary calorimetric chambers of the microcalorimeter constitute separate volumes with the result that mixing of liquid media is impossible, and, hence, the heat of mixture of these media cannot be measured.

There is also known a reactive microcalorimeter (cf. Gill S.T., Chen V., RS I 43 (1972) 774-776; Wadso I, Quarterly Review of Biophysics 3, 4 (1970) 383-427) designed for measuring the heat of mixture of two liquid media at a constant temperature. The microcalorimeter comprises two capillary tubes to supply liquid media, a mixer, a tube to release liquid mixture, a temperature sensor to measure the temperature difference between the supply and release tubes, and a thermostat.

However, this microcalorimeter operates at a constant temperature and does not permit estimates of the effects involved in warming-up, i.e., measurements of the differential calorific capacity.

Therefore, complete physicochemical examination of liquid media, including measurements of the differential calorific capacity of composite media and measurements of the heat of mixture of two media at different temperatures, can be conducted by means of two different instruments: by a scanning microcalorimeter and by a reactive microcalorimeter, whereby measurements taken by two microcalorimeters take much time since the objects of study must be repeatedly transferred from one instrument to the other, and the microcalorimeter operating conditions must be readjusted. Considering that the change of the fixed temperature in a reactive microcalorimeter commonly takes several full days, the fact that the foregoing physicochemical examinations have not been actually practiced till now is quite explicable.

SUMMARY OF THE INVENTION

It is an object of the present invention to provide a differential scanning microcalorimeter, the construction of which will permit both measurements of differential calorific capacity of the examined and reference liquid media, and the heat of mixture of these two media over a wide temperature range.

This object is accomplished in a differential scanning microcalorimeter comprising an adiabatic shell enclosing two capillary calorimetric chambers, the ends extending beyond the adiabatic shell passing through a heat bypass which limits the working volumes of the chambers, with external surfaces of said adiabatic shell, capillary calorimetric chambers and heat bypass mounting thermal sensitive elements and heating elements electrically coupled with temperature controls, wherein, according to the invention, at least one capillary calorimetric chamber is made in the form of two capillary tubes in thermal contact with each other over the full length thereof, wherein tube ends opposite to ends extending from the adiabatic shell are located inside the adiabatic shell, and an end of the other capillary calorimetric chamber opposite to that extending from the adiabatic shell is also enclosed in the adiabatic shell and is connected to the ends of the capillary tubes located inside the adiabatic shell.

It is preferable that the ends of the capillary tubes in the capillary calorimetric chamber which extend from the adiabatic shell, and the end of the other capillary calorimetric chamber which extends from the adiabatic shell, are included into a single assembly whereby they are in thermal contact.

It is furthermore expedient that the thermal contact between the capillary tubes in the capillary calorimetric chamber over the full length thereof, or between the ends thereof extending from the adiabatic shell and the end of the other capillary calorimetric chamber extending from the adiabatic shell, should be established by virtue of direct contact between the walls thereof.

In order that the capillary tubes in the capillary calorimetric chamber be in thermal contact over the full length thereof, it is possible for the tubes to differ in the cross-sectional area thereof, and for the smaller-section tubes be coaxially disposed in the larger-section tubes.

The differential scanning microcalorimeter of this invention permits two types of measurements, viz., measurements of the differential calorific capacity of examined and reference liquid media, and measurement of the heat of mixture of these two liquids at different temperatures, whereby one microcalorimeter combines two separate functions.

BRIEF DESCRIPTION OF THE DRAWINGS

This and other objects of the present invention will become more fully apparent from the following description of preferred embodiments thereof taken in conjunction with the accompanying drawings, wherein:

FIG. 1 is a longitudinal section of a differential scanning microcalorimeter, according to the invention;

FIG. 2 is a longitudinal section of the microcalorimeter according to FIG. 1, wherein both capillary calorimetric chambers are made of two capillary tubes;

DETAILED DESCRIPTION OF THE INVENTION

Figure 4:
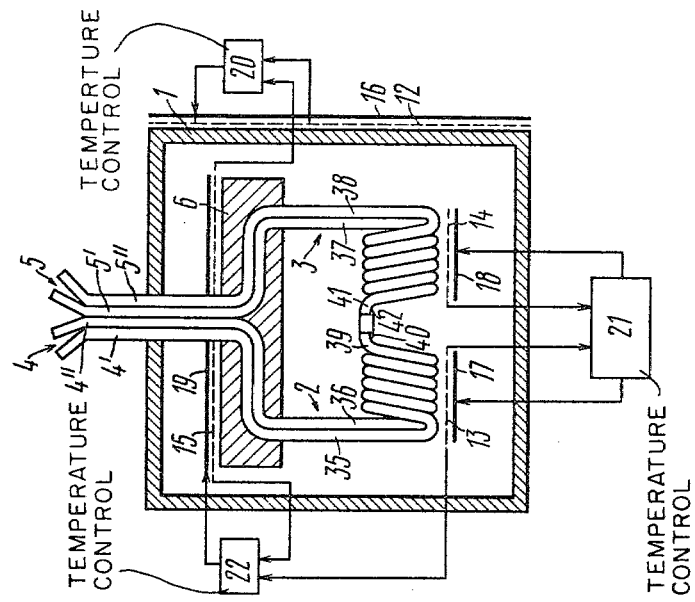
FIG. 4 is a longitudinal section of the microcalorimeter according to the invention, wherein the capillary tubes of both chambers are coiled.

Referring to FIG. 1, a differential scanning microcalorimeter of the present invention comprises an adiabatic shell 1 accommodating two capillary calorimetric chambers 2 and 3, ends 4 and 5 extending from the adiabatic shell 1 passing through a heat bypass 6 in the form of a heat-conducting block serving for limiting the working volumes of these chambers.

One of the capillary calorimetric chambers serves to contain a liquid medium to be tested, and the other is filled with a reference liquid media. The functions of the chambers are reverse if the microcalorimeter is used for measuring the differential calorific capacity of the examined and reference liquid media.

The foregoing embodiment of the microcalorimeter serving for measuring the differential calorific capacity and the heat of mixture of two liquid media incorporates the chamber 3 comprising two capillary tubes 7 and 8, and the chamber 2 formed by a single capillary tube. The tubes 7 and 8 are in thermal contact with each other over the full length thereof. Therefore, this embodiment of the microcalorimeter employs the tubes 7 and 8, the walls of which are in direct contact over the full length thereof.

Ends 9 and 10 of the tubes 7 and 8 opposite to ends 5' and 5" (constituting the common end 5 of the chamber 3) extend beyond the adiabatic shell 1 are enclosed in the adiabatic shell 1. An end 11 of the chamber 2 opposite to the end 4 extending from the adiabatic shell 1 is also enclosed in the adiabatic shell 1 and is connected to the ends 9 and 10 of the tubes 7 and 8.

External surfaces of the adiabatic shell 1, capillary calorimetric chambers 2 and 3, and heat bypass 6 mount thermal sensitive elements 12, 13, 14 and 15, and heating elements 16, 17, 18 and 19. The thermal sensitive elements 12, 13 and 14, and the heating elements 16, 17 and 18 presented in the drawing are shown on the same external surface of the shell 1 and chambers 2 and 3 for the purposes of clarity.

The thermal sensitive element 12 is connected to one input of a temperature control 20, the output of which is applied to the heating element 16. The circuit including the thermal sensitive element 12, heating element 16 and temperature control 20 constitutes a device serving for adjustment of temperature in the adiabatic shell 1. The thermal sensitive elements 13 and 14 are connected to inputs of a temperature control 21, the outputs of which are connected to the heating elements 17 and 18. The circuit of the thermal sensitive elements 13 and 14, heating elements 17 and 18, and temperature control 21 constitutes a device serving for adjustment of temperature in the chambers 2 and 3. The thermal sensitive element 15 is connected to a second input of the temperature control 20 and to one input of a temperature control 22, to the other input of which is connected the thermal sensitive element 13 and the output of which is connected to the heating element 19. The circuit of the thermal sensitive element 15, heating element 19 and temperature control 22 constitutes a device serving for adjustment of temperature in the heat bypass 6.

Turning now to FIG. 2, an alternative embodiment of the microcalorimeter comprises a capillary calorimetric chamber 2 identical to the chamber 3 and including two capillary tubes 23 and 24 thermal contact with each other over the full length thereof. For this purpose, the walls of both tubes 23 and 24 are in direct contact throughout the length thereof.

Ends 25 and 26 of the tubes 23 and 24 opposite to ends 4' and 4" (constituting the common end 4 of the chamber 2) extending beyond the adiabatic shell 1 are enclosed in the adiabatic shell and are connected to the ends 9 and 10 of the tubes 7 and 8.

The foregoing embodiment of the microcalorimeter of the present invention provides for close identity of the two calorimetric chambers which is quite essential during measurements of differential calorific capacity.

Figure 3:
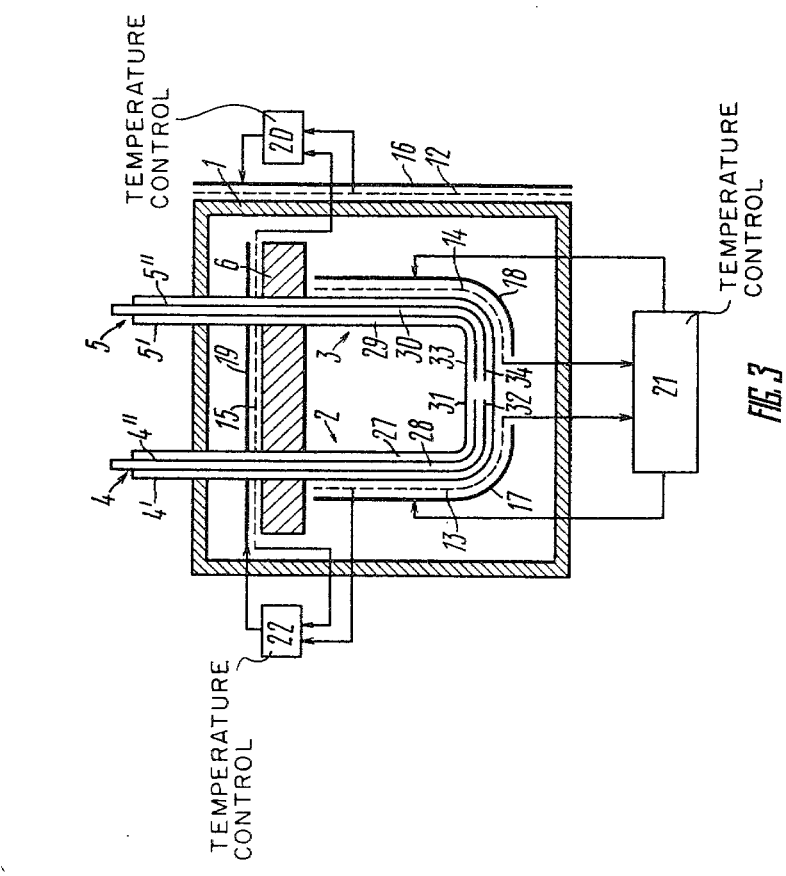
FIG. 3 is a longitudinal section of an alternative embodiment of the microcalorimeter of FIG. 2.

To simplify the microcalorimeter manufacturing procedure and to ensure identity of the calorimetric chambers, it is expedient to devise a microcalorimeter of FIG. 3, wherein the thermal contact between capillary tubes 27 and 28 of the capillary calorimetric chamber 2, and between capillary tubes 29 and 30 of the capillary calorimetric chamber 3 is established over the full length thereof by devising the tubes 27 and 28 in the chamber 2, and the tubes 29 and 30 in the chamber 3 for different cross-sectional areas, and by coaxial disposition of the smaller-section tube 28 in the larger-section tube 27, and of the smaller-section tube 30 in the larger-section tube 29. However, the foregoing microcalorimeter retains all the design features of the microcalorimeters shown in FIGS. 1 and 2, whereby ends 31, 32, 33 and 34 of the tubes 27, 28, 29 and 30 in both chambers 2 and 3, opposite to the respective ends 4', 4", 5' and 5" (constituting the common ends 4 and 5 of the chambers 2 and 3) extending from the adiabatic shell 1 are disposed inside the adiabatic shell 1 and are connected to each other.

The above-mentioned embodiments of the microcalorimeter are furnished with the calorimetric chamber tubes of U-shape.

The embodiment of the microcalorimeter presented in FIG. 4 and designed to minimize the environmental effects on the chambers and, thus, to improve the measuring accuracy, comprises capillary tubes 35 and 36 in the capillary calorimetric chamber 2, and capillary tubes 37 and 38 in the capillary calorimetric chamber 3, which are made in the form of coils.

The ends 4' and 4" of the tubes 35 and 36 extending from the adiabatic shell 1, and the ends 5' and 5" of the tubes 37 and 38 also projecting from the shell 1 constitute a single assembly wherein they are in thermal contact. The thermal contact is established through direct contact between the walls of the tubes 36 and 37. The present embodiment still retains all the design features of the microcalorimeters of FIGS. 1, 2 and 3, whereby ends 39, 40, 41 and 42 of the tubes 35, 36, 37 and 38 in both chambers 2 and 3 opposite to the respective ends 4', 4", 5' and 5" extending from the shell 1 are enclosed in the shell 1 and are connected to each other.

The operating principle of the differential scanning microcalorimeter of the present invention will become easily understandable from the following description.

The differential scanning microcalorimeter according to the invention fulfills two functions:

1. Measurement of differential calorific capacity of examined and reference liquid media;
2. Measurement of heat of mixture of these two media.

1. For measuring the differential calorific capacity, the liquid medium to be tested is supplied through the tube of the chamber 2 (FIG. 1) and is released through the tubes 7 and 8 of the chamber 3. Then the hole in the tube of the chamber 2 is shut off, and the chamber 3 is filled with the reference liquid medium supplied through the tube 7 and released through the tube 8.

To determine the differential calorific capacity, the chambers 2 and 3 are filled with the examined and reference liquid media, and are then heated at equal rates estimated by the thermal sensitive elements 13 and 14. The temperature control 21 of both chambers 2 and 3 monitors the temperature of the heating elements 17 and 18. Then the difference in power consumed for equal heating of each chamber is recorded. During the measuring procedure, the temperature of the heat bypass 6 and the temperature of the adiabatic shell 1 are adjusted by the temperature controls 22 and 20 so as to keep them all the time nearly equal to the temperature of the chambers 2 and 3.

2. For measuring the heat of mixture of two liquid media, the liquids are supplied through both tubes 7 and 8 of the chamber 3, and the mixture is released through the tube of the chamber 2. The liquid media are mixed up at the point where the chambers 2 and 3 communicate, and where the volumes limited by the tubes of the chambers are combined.

The measurements of the heat of mixture of two media are taken when the liquids are constantly flowing through two tubes 7 and 8 of the chamber 3 and when both chambers 2 and 3 are continuously heated by the heating elements 17 and 18, with the difference in power required for heating each chamber estimated like in the previous case.

The operating principle of the microcalorimeter according to FIGS. 2, 3 and 4 is similar to that of the microcalorimeter shown in FIG. 1.

The only difference consists in that the ends 4 and 5 of the chambers 2 and 3 in the microcalorimeter shown in FIG. 4 constitute a single assembly which permits reducing the thermal load of the heat bypass 6 since the medium supplied to the bypass 6 has already adopted the temperature of the bypass 6 which is at thermal contact with the medium returned from the bypass 6. The coil shape of the tubes 35, 36, 37 and 38 in the chambers 2 and 3 contributes to a higher sensitivity of the microcalorimeter as the environmental effects are minimized, and also to fuller integration of the thermal effect in mixing two media, whereby the measuring accuracy is improved.

The differential scanning microcalorimeter proposed herein is versatile as it expands the range of functions of the microcalorimeter in general, and, thus, permits wider examination of physical and chemical properties of liquid media. In addition, the use of the microcalorimeter of the present invention substantially improves the research work efficiency and cuts down the time and the operating costs.

What is claimed is:

1. A differential scanning microcalorimeter, comprising:

an adiabatic shell with an external surface;

a first capillary calorimetric chamber enclosed in said adiabatic shell, provided with an external surface, with a first end extending from said adiabatic shell, and with a second end disposed inside said shell;

a second capillary calorimetric chamber also disposed in said adiabatic shell and provided with an external surface, with a first end extending from said adiabatic shell, at least one of said capillary calorimetric chambers being made in the form of two capillary tubes in thermal contact with each other over the full length thereof; with first ends constituting a first end of said at least one of said chambers extending from said adiabatic shell, and with second ends constituting a second end of said at least one of said chambers enclosed inside said shell and communicating with the second end of the other of said chambers;

a heat bypass disposed in said adiabatic shell, limiting working volumes of said calorimetric chambers and serving to pass said first ends of said chambers extending from said shell;

a first thermal sensitive element located on said external surface of said adiabatic shell;

a second thermal sensitive element located on said external surface of said first capillary calorimetric chamber;

a third thermal sensitive element located on said external surface of said second capillary calorimetric chamber;

a first heating element located on said external surface of said adiabatic shell;

a second heating element located on said external surface of said first capillary calorimetric chamber;

a third heating element located on said external surface of said second capillary calorimetric chamber; and a set of temperature controls electrically coupled with said thermal sensitive elements and said heating elements.

2. A microcalorimeter as claimed in claim 1, wherein said first ends of said capillary tubes in said at least one of said capillary calorimetric chambers, and said first end of said other of said calorimetric chambers constitute a single assembly wherein they are in thermal contact.

3. A microcalorimeter as claimed in claim 2, wherein said thermal contact between said first ends of said capillary tubes in said at least one of said chambers and said first end of said other of said chambers is established by virtue of direct contact between the walls thereof.

4. A microcalorimeter as claimed in claim 1, wherein said thermal contact between said capillary tubes of said at least one of said capillary calorimetric chambers is established over the full length thereof due to direct contact between the walls thereof.

5. A microcalorimeter as claimed in claim 1, wherein said thermal contact between said capillary tubes of said at least one of said capillary calorimetric chambers is established over the full length thereof by the use of tubes of different cross-sectional areas and by disposing the smaller-diameter tubes coaxially in said larger-diameter tubes.

* * * * *